US009255936B2

(12) United States Patent
Hunt et al.

(10) Patent No.: US 9,255,936 B2
(45) Date of Patent: Feb. 9, 2016

(54) SAMPLE STORAGE CASSETTE FOR ULTRA-LOW OR CRYOGENIC TEMPERATURES

(75) Inventors: Frank Hunt, Shrewsbury, MA (US);
Julian Warhurst, Ashland, MA (US);
Bruce Zandi, Lexington, MA (US);
Robert Cloutier, Lancaster, MA (US)

(73) Assignee: Hamilton Storage Technologies, Inc., Franklin, MA (US)

( * ) Notice: Subject to any disclaimer, the term of this patent is extended or adjusted under 35 U.S.C. 154(b) by 922 days.

(21) Appl. No.: 13/228,662

(22) Filed: Sep. 9, 2011

(65) Prior Publication Data
US 2012/0060541 A1 Mar. 15, 2012

Related U.S. Application Data (60) Provisional application No. 61/381,832, filed on Sep. 10, 2010.

(51) Int. Cl.
*A47B 96/04* (2006.01)
*G01N 35/04* (2006.01)
(Continued)

(52) U.S. Cl.
CPC .............. *G01N 35/04* (2013.01); *A01N 1/0236* (2013.01); *A01N 1/0252* (2013.01); *B01L 7/50* (2013.01);
(Continued)

(58) Field of Classification Search
CPC .... A01N 1/0236; A01N 1/0252; B01L 17/50; B01L 19/06; B01L 2200/026; B01L 2300/021; B01L 2300/04; B65D 1/00; F17C 3/085; F25D 25/00; F25D 25/04; G01N 35/0099; G01N 35/04; G01N 2035/00346; G01N 2035/00435; G01N 2035/042; G01N 2035/0425; G01N 2035/0462; G01N 1/42
USPC ........... 312/402, 404, 408, 348.3, 330.1, 264, 312/265, 257.1, 107, 108, 198, 199, 297
See application file for complete search history.

(56) References Cited

U.S. PATENT DOCUMENTS 129,688 A * 7/1872 Smith ........................... 312/107
461,378 A 10/1891 Allen
(Continued)

FOREIGN PATENT DOCUMENTS

EP 0725133 12/1998
EP 1074488 9/2002
(Continued)

OTHER PUBLICATIONS

International Preliminary Report on Patentability, PCT/US2011/050955, date of mailing Mar. 21, 2013.
(Continued)

*Primary Examiner* — Daniel J Troy
*Assistant Examiner* — Timothy M Ayres
(74) *Attorney, Agent, or Firm* — Andrus Intellectual Property Law, LLP (57) ABSTRACT

A storage cassette including a plurality of generally vertical compartments for storing sample tube racks and/or SBS formatted plates is constructed to be flexible along its substantially vertical axis thereby facilitating reliable robotic placement and retrieval of the cassette from nesting tubes located within a horizontal freezer compartment. Insulated walls and solid shelves minimize heat transfer from storage racks or plates placed in the storage cassette when the cassette is removed from an ultra-low temperature or cryogenic freezer. The outer walls of the cassette includes mechanical indexing locations to ensure appropriate positioning when robotically removing storage racks or plates from the cassette.

20 Claims, 8 Drawing Sheets

(51) Int. Cl.
| | |
|---|---|
| *A01N 1/02* | (2006.01) |
| *B01L 7/00* | (2006.01) |
| *B65G 1/00* | (2006.01) |
| *F17C 3/08* | (2006.01) |
| *F25D 25/00* | (2006.01) |
| *B01L 9/06* | (2006.01) |
| *F25D 25/04* | (2006.01) |
| *G01N 1/42* | (2006.01) |
| *G01N 35/00* | (2006.01) |

(52) U.S. Cl.
CPC . *B65G 1/00* (2013.01); *F17C 3/085* (2013.01); *F25D 25/00* (2013.01); *B01L 9/06* (2013.01); *B01L 2200/026* (2013.01); *B01L 2200/04* (2013.01); *B01L 2300/021* (2013.01); *B01L 2300/04* (2013.01); *F25D 25/04* (2013.01); *G01N 1/42* (2013.01); *G01N 35/0099* (2013.01); *G01N 2035/00346* (2013.01); *G01N 2035/00435* (2013.01); *G01N 2035/042* (2013.01); *G01N 2035/0425* (2013.01); *G01N 2035/0462* (2013.01)

(56) References Cited

U.S. PATENT DOCUMENTS

| | | | |
|---|---|---|---|
| 1,001,524 A | | 8/1911 | Holcomb |
| 1,508,259 A | * | 9/1924 | Stafford ............... 312/195 |
| 4,413,867 A | * | 11/1983 | Mosebrook et al. .......... 312/111 |
| 5,735,587 A | | 4/1998 | Malin et al. |
| 6,068,437 A | | 5/2000 | Boje et al. |
| 6,129,428 A | | 10/2000 | Helwig et al. |
| 6,255,614 B1 | | 7/2001 | Yamakawa et al. |
| 6,397,620 B1 | | 6/2002 | Kelly et al. |
| 6,435,582 B1 | | 8/2002 | DaSilva et al. |
| 6,467,285 B2 | | 10/2002 | Felder et al. |
| 6,478,524 B1 | | 11/2002 | Malin |
| 6,536,859 B1 | | 3/2003 | Bathe |
| 6,568,770 B2 | | 5/2003 | Gonska et al. |
| 6,581,395 B2 | | 6/2003 | Felder et al. |
| 6,688,123 B2 | | 2/2004 | Felder et al. |
| 6,694,767 B2 | | 2/2004 | Junca et al. |
| 6,718,776 B2 | | 4/2004 | Wessling et al. |
| 6,752,479 B2 | | 6/2004 | Ferger et al. |
| 6,834,920 B2 | * | 12/2004 | Landsberger et al. ..... 312/257.1 |
| 6,941,762 B2 | | 9/2005 | Felder et al. |
| 6,990,819 B2 | | 1/2006 | Darling |
| 7,013,197 B2 | | 3/2006 | Melching et al. |
| 7,013,198 B2 | | 3/2006 | Haas |
| 7,059,138 B2 | | 6/2006 | Bonaquist et al. |
| 7,214,022 B2 | | 5/2007 | Melching |
| 7,227,746 B2 | | 6/2007 | Tanaka et al. |
| 7,290,396 B2 | | 11/2007 | Rampersad et al. |
| 7,314,341 B2 | | 1/2008 | Malin |
| 7,494,168 B1 | | 2/2009 | Miller |
| 7,527,764 B2 | | 5/2009 | Angelantoni et al. |
| 7,635,246 B2 | | 12/2009 | Neeper et al. |
| 7,648,321 B2 | | 1/2010 | Neeper et al. |
| 7,793,842 B2 | | 9/2010 | Neeper et al. |
| 7,861,540 B2 | | 1/2011 | Cloutier et al. |
| 8,083,994 B2 | | 12/2011 | Neeper et al. |
| 8,176,747 B2 | | 5/2012 | Howard et al. |
| 2002/0171332 A1 | * | 11/2002 | Skov et al. .................... 312/107 |
| 2002/0198610 A1 | | 12/2002 | Malin et al. |
| 2003/0233842 A1 | | 12/2003 | Junca et al. |
| 2004/0154322 A1 | | 8/2004 | Felder et al. |
| 2004/0213651 A1 | | 10/2004 | Malin |
| 2004/0258566 A1 | | 12/2004 | Smith |
| 2005/0028538 A1 | | 2/2005 | Darling |
| 2005/0069401 A1 | | 3/2005 | Malin |
| 2005/0188705 A1 | | 9/2005 | Jones et al. |
| 2006/0053825 A1 | | 3/2006 | Owen et al. |
| 2006/0105450 A1 | | 5/2006 | Owen |
| 2006/0289371 A1 | | 12/2006 | Malin |
| 2007/0064383 A1 | | 3/2007 | Tanaka et al. |
| 2009/0101738 A1 | | 4/2009 | Stitt et al. |

FOREIGN PATENT DOCUMENTS

| | | |
|---|---|---|
| EP | 1253817 | 10/2002 |
| EP | 1211197 | 2/2003 |
| EP | 1441026 | 7/2004 |
| EP | 1443101 | 8/2004 |
| EP | 1634496 | 3/2006 |
| EP | 1639892 | 3/2006 |
| EP | 1721964 | 11/2006 |
| EP | 1757883 | 2/2007 |
| EP | 1354028 | 9/2007 |
| EP | 0853657 | 12/2007 |
| EP | 1477813 | 2/2008 |
| GB | 531 578 | 1/1941 |
| JP | 2007-010531 | 1/2007 |
| JP | 2007-30390 | 11/2007 |
| SE | 184 048 | 5/1963 |
| WO | 85/00422 | 1/1985 |
| WO | 98/05753 | 2/1998 |
| WO | 02059251 | 8/2002 |
| WO | 2006074568 | 7/2006 |
| WO | 2006074569 | 7/2006 |

OTHER PUBLICATIONS

REMP, "Small-Size Store (SSS)", pp. 1-2, http://www.remp.com/index.asp?cms=22.
REMP, "Tube Punching Module (TPM)", p. 1, http://www.remp.com/index.asp?cms=33, Jan. 2008.
RTS Life Sciences, "RTS A2—Automated Sample Management for Small Libraries/Sample Collections", pp. 1-3, http://www.rtslifescience.com/html/A2-sample-store.htm, Feb. 26, 2009.
LiCONiC AG, "Tube Picker", p. 1, http://www.liconic.com/products/plate-management/plate-manag.html, Jan. 15, 2008.
LiCONiC AG, "Tube Boxer", p. 1, http://www.liconic.com/products/plate-management/tube-boxer.html, Mar. 24, 2009.
The Automation Partnership, "Polar—System Overview", pp. 1-2, http://www.automationpartnership.com/tap/sms/Polar.htm, Mar. 24, 2009.
Matrical Bioscience, "MiniStore", pp. 1-2, http://www.matrical.com/MiniStore.php, Feb. 26, 2009.
Nexus Biosystems, "Universal Store—Compound Storage System", pp. 1-2, http://www.nexusbio.com/Products/SampleManagement/compound_storage.php, Feb. 26, 2009.
TTP Labtech, "comPOUND", pp. 1-2, http://www.ttplabtech.com/products/compound/index.html, Feb. 26, 2009.
Biomicrolab, "XL20 Tube Handler", pp. 1-2, http://www.biomicrolab.com/products_XL20.htm, Feb. 26, 2009.
Honeywell, HIH-400 Series, pp. 1-8, www.honeywell.com/sensing, Minneapolis, MN, Jan. 2007.
RTS Group, "Compound Management", http://rtslifescience.com/html/compound-management.htm, pp. 1-14, 2005, Jan. 15, 2008.
Matrical, "MatriStore—Automated Compound Storage and Retrieval System", "MatriPress—Microwell plate storage freezer rack" http://www.matrical.com/MatriStore2.php, pp. 1-6, Spokane, WA 2007, Jan. 16, 2008.
LiCONiC Instruments, "Product Overview", pp. 1-2, Woburn, MA, Jul. 19, 2007.
Thermo Scientific, "Automated Sample Library at -80C-Thermo Scientific", http://www.thermo.com/com/dcs/product/detail/10120038,00.html, pp. 1-2, 2007, Jan. 15, 2008.
Tecan Group Ltd.—News, "Automated production of microfluidic devices with the Freedom EVO/REMP Small-Size Store Factory", http://www.tecan.com/page.content/index.asp?MenuID, pp. 1-2, Switzerland, 2008, Jan. 15, 2008.
REMP, "Sample Safe", pp. 1-2, Mannedorf, Switzerland, Jan. 2007.
REMP, "Storage Family", pp. 1-6, Mannedorf, Switzerland, Jan. 2007.
Oriental Motor U.S.A. Corp., "2-Phase Stepping Motor", www.orientalmotor.com, pp. 1-2, Torrance, CA, Jan. 22, 2008.

(56) References Cited

OTHER PUBLICATIONS

Applied Motion Products, "Motors, Motion Control Products, Drives and Controls", http://www.applied-motion.com/products/servo/motors/NMseries.php., pp. 1-6, 2006, Jan. 22, 2008.
ANSI/SBS Jan. 2004, "Footprint Dimensions", American National Standards Institute, Society for Biomolecular Sciences, pp. 1-8, Jan. 25, 2006.
AIRTX International, "Air Knives:Aluminum 85000 Series", http://www.airtxinternational.com/catalog/82000/php., pp. 1-4, Jan. 22, 2008.
LiConic Instruments, -80C Degree Tube Stores, http:/liconic.com/products/plate-management/tube-store-80.php, Jul. 10, 2012.
TTPLabTech, Arktic compact, automated biobanking, TTP Labtech strengthens automated sample management for biobanking with arktic: Bringint biobanking to any lab, any size at IQPC, http://ttplabtech.com/news-media/news/ttp-labtech, Jul. 10, 2012.
LiConic Instruments, STC12k5, http:/liconic.com/products/plate-management/tube-store-80.php, Jul. 10, 2012.
LiConic Instruments, STC3k5, http:/liconic.com/products/plate-management/tube-store-80.php, Jul. 10, 2012.
LiConic Instruments, STC7k5, http:/liconic.com/products/plate-management/tube-store-80.php, Jul. 10, 2012.
Matrical Bioscience, NitroStore Mars & Saturn—Biobank/Biorepository, -80C to -160C Automated Sample, Storage, Management, & Retrieval Systems, http://matrical.com/Biobank_Biorepsosiory.php, Jul. 10, 2012.

\* cited by examiner

SAMPLE STORAGE CASSETTE FOR ULTRA-LOW OR CRYOGENIC TEMPERATURES

CROSS REFERENCE TO RELATED APPLICATIONS

This application claims priority to U.S. Provisional Patent Application No. 61/381,832, filed on Sep. 10, 2010 entitled "Large Automated Storage and Retrieval System for Storing Biological or Chemical Samples at Ultra-Low or Cryogenic Temperatures".

FIELD OF THE INVENTION

The invention relates to automated storage and retrieval systems for ultra-low temperature or cryogenic freezers used primarily to store biological or chemical samples. More specifically, the invention is directed to a storage cassette for transporting multiple sample tube storage racks and/or sample storage plates and for holding the sample storage racks and/or plates within horizontal freezer compartments.

BACKGROUND OF THE INVENTION

Many biological and chemical samples are stored at or below freezing temperatures. Generally speaking, a regular freezer operates from −5° C. to −20° C., an ultra-low temperature freezer operates from about −50° C. to −130° C. (preferably about −80° C.) and a cryogenic freezer operates from about −140° C. to −196° C. (the boiling point of liquid nitrogen). Most biological samples stored in ultra-low temperature or cryogenic systems are contained in sealed plastic laboratory tubes held in tube storage racks in arrays of, for example, 48, 96 or 384 tubes. In the art, it is known to robotically store tube storage racks on shelves or in removable storage cassettes within ultra-low temperature or cryogenic freezer compartments. Known storage cassettes typically have vertically aligned metal shelves with metal sidewalls. The top of the cassette usually has a handle for manual or robotic lifting of the cassette. A typical height of the prior art storage cassettes is about 3 feet in order to enable manual handling of the cassettes. Front and rear walls are typically open to allow access to the storage tube racks. Some cassettes have open shelves and some have closed shelves.

The present invention as mentioned is directed to storage cassettes for holding sample storage tube racks or plates within horizontal freezer compartments and for robotically transporting sample storage tube racks and plates into and from the freezer compartments. The primary objectives of the invention are to provide sample safety and thermal integrity while moving the storage cassettes from and into the freezer compartments. In order to accommodate a large number of samples, storage cassettes made in accordance with the invention can typically be about six feet long with, for example, twenty (20) or more shelves for holding tube storage racks and/or plates, although the cassettes can be made shorter (e.g. 3 feet) or even taller if less or more storage capacity per cassette is desired. One of the problems that must addressed when robotically transporting storage cassettes is that frost formation and thermal expansion and contraction can lead to difficulties when placing storage cassettes into storage racks in ultra-low temperature or cryogenic freezers. To address this problem, the invention provides a storage cassette that can reliably be inserted and removed from freezer compartments despite dimensional differences caused by thermal contraction and expansion, robotic misalignment, relatively minor frost formation or other difficulties that can be encountered. Reliability of insertion and removal is important because the time to remedy a jam can result in sample temperature rise which in turn can compromise sample integrity. The preferred embodiment of the invention includes not only features to facilitate reliable insertion and removal of storage cassettes from freezer compartments, but also features to reduce temperature rise in samples when the cassette is pulled from the freezer compartment.

SUMMARY OF THE INVENTION

A storage cassette constructed in accordance with an exemplary embodiment of the invention includes a plurality of spaced, shelves stacked generally vertically, each for holding a sample tube storage rack or a sample storage plate. Separate side wall partitions made of thermally insulating, rigid material span between the shelves to form a plurality of compartments generally vertical to one another. Each of the compartments contains at least one opening to allow storage racks or plates to be placed in the compartment on the shelf and removed from the compartment. The cassette is generally flexible along its substantially vertical axis. The storage cassette in the exemplary embodiment is capable of storing 20 or more, e.g. 26, tube storage racks and is about six feet in height, although as mentioned above, it is contemplated that a storage cassette constructed in accordance with the invention may be shorter (e.g. 3 feet) and have fewer shelves such as 15 shelves, or even be taller and contain more shelves. The flexibility enables the cassette to bend as necessary to facilitate reliable placement of the cassette into and removal of the cassette from nesting tubes located in horizontal freezer compartments. In this regard, it is desirable that the freezer compartment contain an array of cassette storage nesting tubes each comprising a vertically oriented, rectangular tube to guide the cassette over its entire length into the freezer bay. The nesting tubes are preferably made of aluminum and have sidewalls containing air flow openings to promote cold air circulation throughout the freezer and facilitate rapid cooling of samples stored in the cassettes.

Each cassette preferably includes an insulated cap located above the plurality of vertically oriented compartments. The preferred caps includes a top plate having an upwardly extending retrieval catch for an automatic transfer robot and also guide holes for guide pins on the automated transfer robot to ensure that the cassette properly aligns with the robot to engage the retrieval catch and lift the cassette. The outer walls of the cassette preferably include mechanical indexing dimples to ensure appropriate positioning when robotically removing storage racks or plates from the cassette. The bottom of the cassette preferably includes tapered and rigid guide legs that extend downward from the bottom of the cassette. The purpose of the tapered rigid legs is to facilitate proper alignment of the bottom of the cassette with the top of nesting tubes within the freezer compartment when placing the cassette into the freezer. Under normal operation, the storage cassettes will not normally have to be fully removed in order to remove or place a sample tube storage rack or a storage plate within a compartment in the cassette. The purpose of the guide legs is, however, to facilitate placement of the cassette into a respective nesting tube when the storage cassette needs to be fully removed and placed in the same or another location. Preferably, the guide legs on the cassette do not stand on the bottom of the freezer. Rather, it is desirable that the bottom of the freezer not be horizontal and be contoured to facilitate drainage after defrosting. Desirably, support members are located near the bottom of the nesting tubes, such as horizontal support rods spanning through rows of nesting tubes, in order to hold the respective cassettes above the bottom of the freezer such that the caps of the cassettes are held at the same or substantially the same horizontal height. The space in the freezer below the cassettes facilitates air circulation which also improves the efficiency of cooling samples stored in the cassettes.

As mentioned, it is desirable that the cassette be flexible along its substantially vertical axis. In the exemplary embodiment, this is achieved by connecting the shelf partition plates and the insulated sidewall partitions with wire to top and bottom plates of the cassette. Desirably, the compartments are generally rectangular and wire passes through the four corners of the components to provide a robust yet flexible, generally vertical column of compartments. The flexible nature of the storage cassette greatly enhances the ability of the cassette to be robotically placed into the nesting tubes in a reliable manner. This is particularly important because jams have the potential to mechanically harm samples, and perhaps more importantly require time to remedy which can lead to the warming of samples in the cassette or in the freezer if the lid is removed.

The use of thermally insulated sidewall partitions in the cassette as well as the use of fully closed shelves protects samples stored in the cassette from temperature fluctuations not only when the cassette is removed from the ultra-low temperature or cryogenic freezer but also when warm samples are placed into the freezer in an adjacent location. The preferred side wall partition includes a front opening to allow storage racks or plates to be placed in or removed from the compartment, and also includes a smaller opening in the rear compartment wall to allow robotic access from the rear. Closed shelves are particularly desirable to preserve the thermal integrity of samples when the cassettes are removed from the freezer bay. It has been found that the use closed shelves block a convection chimney effect from forming when the cassette is removed from the freezer bay and greatly reduces temperature rise in samples stored in the cassette.

Aspects of the invention are also directed to features for ensuring that the tube storage racks and/or plates do not mistakenly fall or become ajar from the respective compartments in the cassette. In this regard, it is desirable that each shelf include one or more upwardly extending lips on the front edge near the front opening through which the storage racks or plates are placed into and removed from the compartment. In order to remove the storage rack from the compartment, a robot must lift the storage rack and/or plate above the front lip(s). It is also desirable to limit the height of the compartment so that there is minimal clearance, for example only about one-quarter of an inch, above the top of the storage tubes in the rack when the rack is lifted above the lip. Further, it is desirable that the nesting tubes within the freezer compartment each include a vertically longitudinal bar that protrudes inward from a sidewall of the nesting tube in a position corresponding to the front openings of the compartments on the cassette. Desirably, the bar extends substantially the entire vertical length of the sidewall of the nesting tube so that the bar maintains the storage racks and or plates fully within the compartment over the entire length of the cassette, thereby substantially eliminating the risk of a storage rack or plate from moving out of its compartment, even partially, when the cassette is being removed or placed into the nesting tube even in the case of a mechanical jam.

Other objects and features of the invention may be apparent to those of ordinary skill in the art upon reviewing the following drawings and description thereof.

DETAILED DESCRIPTION OF THE DRAWINGS

Figure 1:
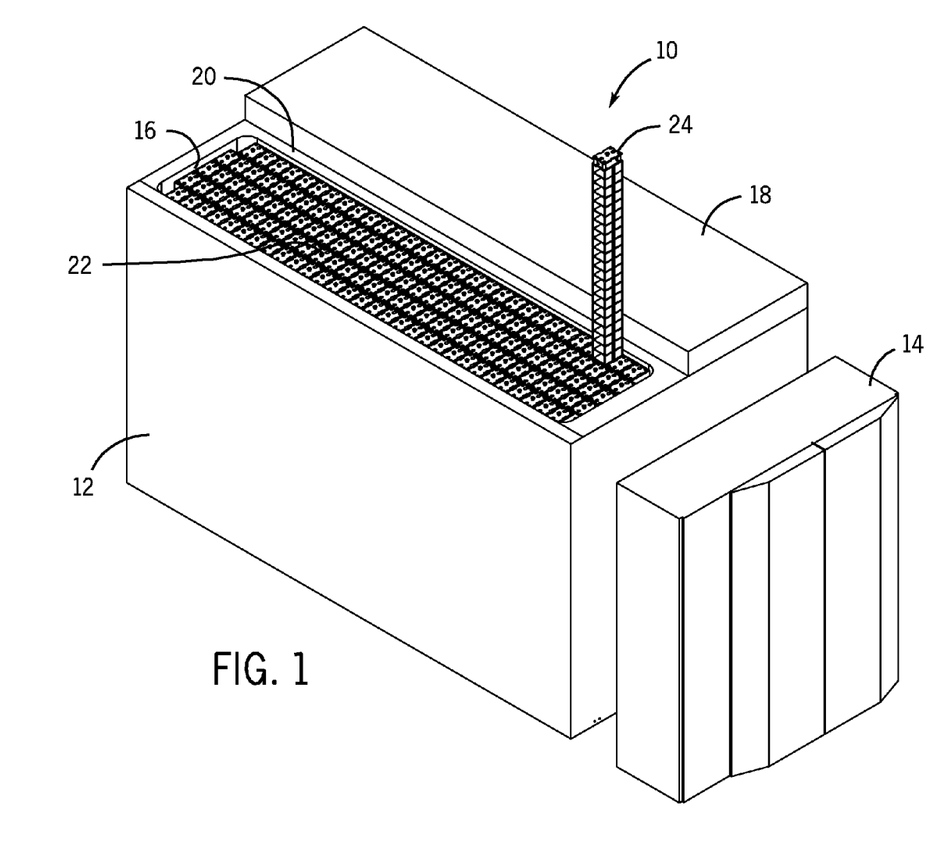
FIG. 1 is a perspective view of a horizontal, ultra-low temperature or cryogenic freezer system constructed in accordance with an exemplary embodiment of the invention for holding sample storage tube racks and sample storage plates within the freezer compartment and for transporting sample storage tube racks and sample storage plates into and from the freezer compartment.
Figure 11:
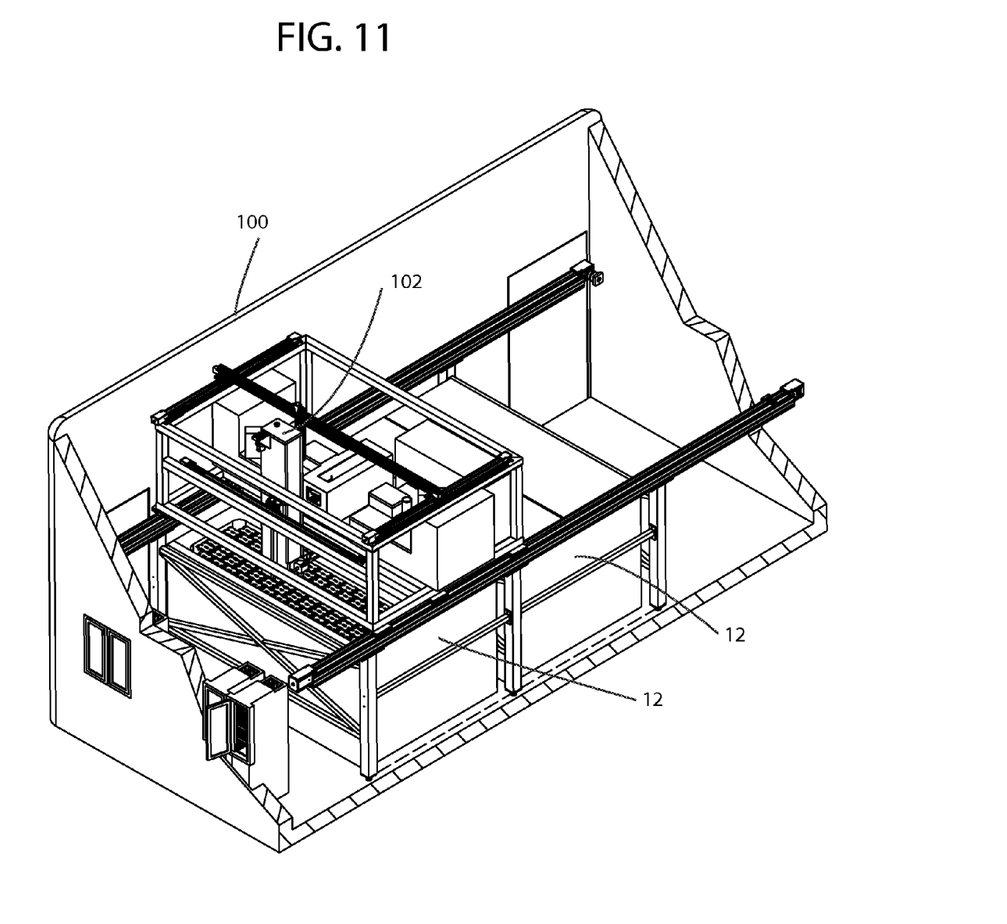
FIG. 11 is a perspective view of a system for holding sample storage tube racks, showing horizontal freezers and an automated transfer robot located in a refrigerated enclosure.

FIGS. 1-8 illustrate an exemplary embodiment of the invention which is directed to a system 10 including a horizontal freezer 12 for storing biological or chemical samples typically in SBS format tube storage racks and/or storage plates. Typically, the freezer chest 12 will be located within a refrigerated enclosure 100 (FIG. 11) that is maintained at a low temperature of approximately −15° C. to −30° C., such as described in Ser. No. 13/228,651; Publication No. US 2012/00605391A1, entitled "Cassette Puller", filed on even date herewith, now abandoned, and claiming priority to provisional application no. U.S. 61/381,832 filed on Sep. 9, 2010, entitled "Large Automated Storage and Retrieval System for Storing Biological or Chemical Samples at Ultra-Low or Cryogenic Temperatures" which is incorporated herein by reference. It is contemplated that multiple horizontal freezer chests like freezer chest 12 will be located within the refrigerated enclosure 100. Each freezer chest 12 preferably includes a storage compartment preferably maintained at about −80° for ultra-low temperature applications, although many aspects of the invention are useful even if the freezer compartment is maintained at other temperatures such as −50° to −90° C. or colder for example, about −135° C. (ultra-low temperatures) or cryogenic temperatures (e.g. about −140° C. to 196° C.). Biological or chemical samples, typically stored in plastic tubes held in storage tube racks or stored in wells within sample storage plates, are stored within the refrigerated compartment within the freezer chest. Refrigeration units 14 for the respective freezer chests 12 are located on the exterior of the refrigerated enclosure. Desirably, the freezer chest 12 includes two bays 16 separated by refrigerated wall 20. FIG. 1 shows a lid 18 covering one of the hays, and freezer bay 16 from which the lid, has been removed to provide access to storage cassettes 24 located within the bay 16 by an automatic transfer robot 102, FIG. 11. The preferred automatic transfer robot 102 is shown in FIG. 11 and described in the above incorporated U.S. patent application Ser. No. 13/228,651, now abandoned, entitled "Cassette Puller" filed on even date herewith and claiming priority to provisional application no. U.S. 61/381,832 filed on Sep. 9, 2010.

Figure 6:
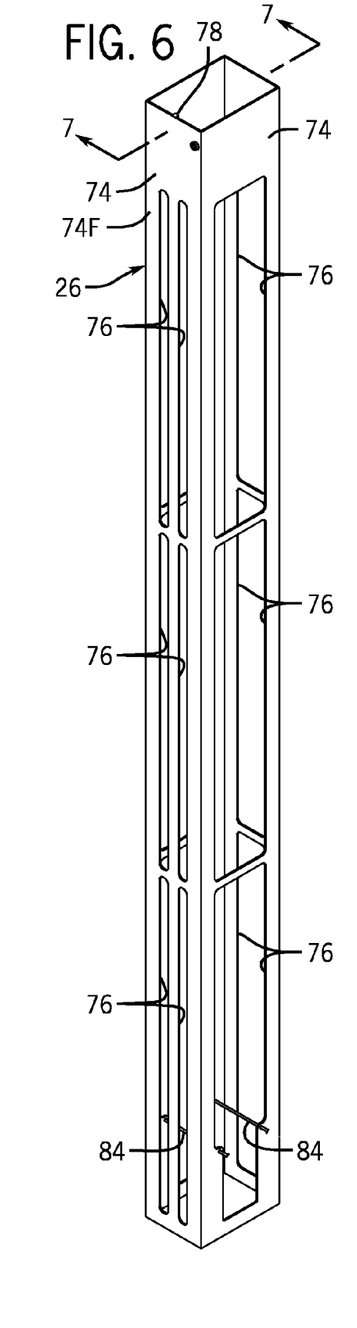
FIG. 6 is a perspective view of a nesting tube constructed in accordance with an exemplary embodiment of the invention and forming part of a nest of such tubes placed in a freezer compartment as illustrated in FIG. 1.

A nest 22 of aluminum nesting tubes sits within the freezer bay 16. The nesting tubes are arranged in rows and in the exemplary embodiment shown on FIG. 1, there are 153 nesting tubes in each bay, although the size of the freezer bays and the number of nesting tubes can vary without departing from the spirit of the invention. Refrigeration coils are contained in the walls surrounding each of the refrigeration bays 16 including the wall 20 between the bays, in order to facilitate even and controlled refrigeration within the respective freezer bays 16. Referring briefly to FIG. 6, a plurality of the exemplary nesting tubes 26 shown in FIG. 6 are preferably connected together such as by rivets or welding to form the nest 22 contained within the freezer bay 16.

Figures 2, 3:
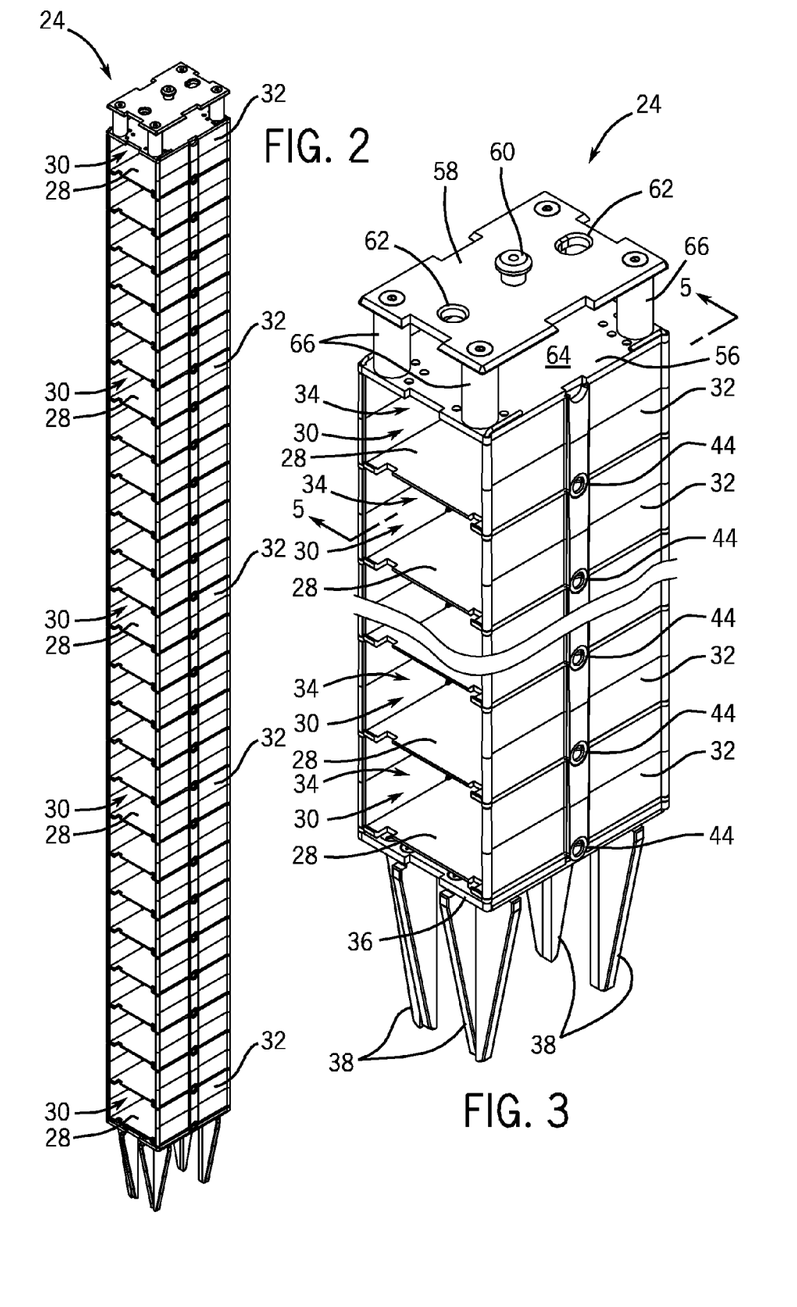
FIG. 2 is a perspective view of a storage cassette constructed in accordance with an exemplary embodiment of the invention configured to be used with the horizontal, ultra-low temperature or cryogenic freezer system shown in FIG. 1.
FIG. 3 is a detailed view of the upper and lower portions of the storage cassette illustrated in FIG. 2.

Referring now to FIG. 2, a storage cassette 24 constructed in accordance with the invention includes a plurality of spaced shelves 28. The construction of the cassette 24 allows for robust handling of the cassette 24 with cost effective components. The spaced shelves 28 are preferably made of aluminum, and provide a closed floor for the respective compartments 30 in the cassette 24 that hold the sample tube storage racks or storage plates. The shelves 28 are oriented generally vertical to one another, but as discussed in more detail below, the storage cassette 24 is flexible along its vertical axis. Separate side wall partitions 32 span between the shelves 28 to form the compartments 30 for storing the sample tube storage racks and storage plates. The side wall partitions 32 are made of thermally insulating rigid material, such as molded polypropylene, although other thermally insulating plastics that can withstand the temperature changes between the freezer bay and environment outside of the freezer can be used. Referring in particular to FIGS. 2 and 3, each of the compartments 30 includes an opening 34 to allow storage tube racks or plates to be placed into the compartment 30 on the respective shelf 28 and also removed from the compartment 30. Typically, the placement and removal of the storage racks and/or storage plates will be via an automatic robot 102 (FIG. 11) located in the environment in which the freezer 12 is located, see, the above incorporated, patent application entitled "Cassette Puller" Ser. No. 13/228,651, now abandoned.

The cassette 24 shown in FIG. 2 includes 30 compartments and stands roughly six feet tall (although, as mentioned, the height of the cassette and number of shelves in the cassette can vary without departing from the spirit of the invention). While the relatively tall height of the cassette 24 enables a large number of samples to be stored in a single cassette, the tall height also introduces challenges in robotically handling the cassette 24. Several features of the cassette 24 are designed to facilitate reliable placement of the cassette 24 into the respective nesting tube 26 in the freezer 12.

Figure 4:
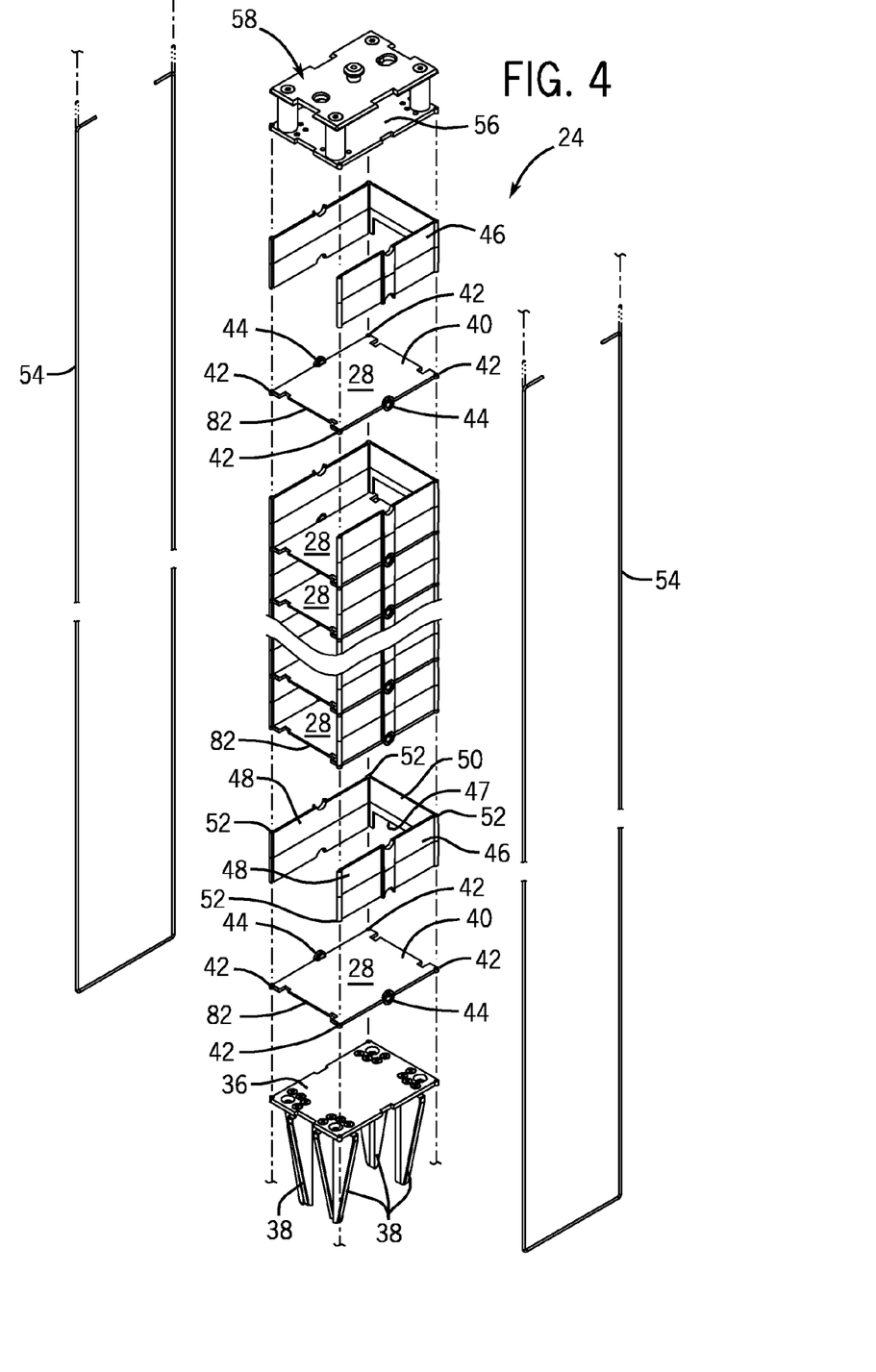
FIG. 4 is an assembly view of the storage cassette illustrated in FIG. 2.

FIG. 4 is an assembly drawing of the exemplary cassette 24. Guide legs 38 are attached to a bottom plate 36 and extend downward from the bottom plate 36. The purpose of the guide legs 38, as mentioned, is to help guide the cassette 24 into the appropriate nesting tube 26 when the storage cassette 24 has been completely removed. As shown best in FIG. 7, the guide legs 38 do not rest on the bottom surface of the freezer bay 16.

Still referring to FIG. 4, each shelf 28 constitutes part of a partition shelf plate 40 which are generally rectangular aluminum plates. Wire pass through holes 42 are located in each corner of the partition shelf plates 40. The front and the rear edges of the plate 40 include notches to facilitate robotic handling of racks or plates stored in respective compartments. Mechanical referencing or indexing dimples 44 are located on each side edge of the partition shelf plates 40. The referencing or indexing dimples 44 provide a mechanical indent for the cassette puller, or other automated robot, to verify and adjust the precise location of the cassette 24 once it has been removed from the freezer 12 and presented in a location for the removal of a tube storage rack or plate into a respective compartment or the placement of a storage rack or plate into the respective compartment 30. The thermally insulated sidewall partitions 46 as mentioned span between the partition shelf plates 40. The thermally insulated partitions 46 includes two sidewalls 48 and rear wall 50, preferably all molded as an integral component. The four corners of the sidewall partitions 46 include wire pass through holes 52. When the cassette 24 is assembled, wire 54 extends vertically through the pass through holes 42 of the shelf partition plates 40 and the pass through holes 52 of the sidewall partitions 46. More specifically, the wire 54 as shown in FIG. 4 passes through openings at the corner of the bottom plate 36 up through each shelf partition plate 40 and sidewall partition 46 sequentially until the wire reaches a plate 64 on the cap 56 of the cassette 24 through which the wire 54 is secured. The wire assembled construction is robust, yet flexible. Stainless steel wire having a diameter of 3/32" is suitable for this application. As mentioned the flexibility along longitudinal axis allows the storage cassette 24 to physically adjust to accommodate dimensional obstructions when placing the cassette 24 into or removing the cassette from a nesting tube 26.

Referring to FIG. 3, the storage cassette 24 as mentioned includes a cap 56. The cap 56 includes a top plate 58 having a retrieval catch 60 that is adapted to be engaged by an automated robot 102 (FIG. 11) for lifting the storage cassette 24 from the nesting tubes 26, transporting the storage cassettes 24 and placing the storage cassettes 24 into the nesting tubes 26. The retrieval catch 60 extends upward from the top plate 58 and has generally circular head. This particular configuration for the retrieval catch 60 shown in the figures is particularly well-suited for engagement with a robotic cassette puller as described in the above incorporated, patent application Ser. No. 13/228,651, now abandoned, entitled "Cassette Puller". In a broad aspect of the present invention, the retrieval catch 60 need not have a configuration compatible with the cassette puller in the above-identified co-pending patent application, but can be configured to be engaged by another type of automated robot or even by hand. The top plate 58 of the cassette cap 56 also includes guide holes 62 designed to receive guide pins extending downward from the cassette puller described in the above incorporated, co-pending patent application. The purpose of the guide pins and the guide holes 62 is to align the cassette 24 in the nesting tube with the cassette puller before engaging the cassette 24. The cap 56 includes a bottom plate 64 to which as mentioned the wire 54 is attached. The top plate 58 of the cap 56 is spaced above the bottom plate 64 of the cap 56 and provides clearance for the guide pins. The top plate 58 is attached to the bottom plate 64 with screws at the four corners passing through insulated standoffs 66. Although not shown in the drawings, it is likely in a −80 freezer application that insulation will be located between the top plate 58 and bottom plate 64 of the cap 56. Note that for purposes of manufacturing convenience, the configuration of the bottom plate 64 for the cap 56 is the same as the bottom plate 36 at the bottom of the cassette. Thus, the screw holes that appear in bottom plate 64 of the cap 56 serve no purpose on the cap inasmuch the holes are used to attach the guide legs 38 to the bottom of the cassette 24.

Figure 5:
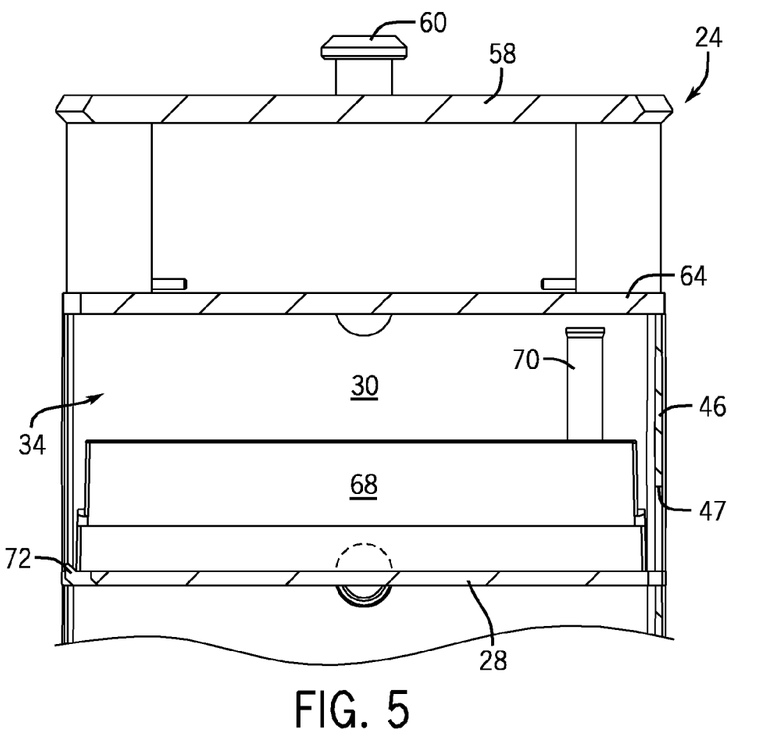
FIG. 5 is a view taken along line 5-5 in FIG. 3.

Referring now to FIG. 5, a sample storage tube rack 68 containing one sample storage tube 70 is contained within a compartment 30 of the storage cassette 24. Normally, the storage tube rack 68 would be completely or partially filled with storage tubes 70 although only one storage tube is shown for purposes of illustration. The storage rack 68 sits on shelf 28. The rear portion of the insulating sidewall 46 includes an opening 47 to allow robotic access from the rear of the storage cassette 24 when the cassette is removed from the freezer. A leading edge of the shelf 28 near the large opening 34 includes a lip 72. The lip 72 helps to prevent the storage rack 68 from inadvertently sliding forward on the shelf 28. In order to remove the storage rack 68 from the compartment 30 it is therefore necessary to lift the storage rack 68 above the front lip 72. The height of the compartment 30 is preferably customized to the specific type of storage rack 68 and tube 70 intended to be stored in the compartment 30, and is selected so that there is only slight clearance above the storage tube 70. For example, a suitable height for the front lip would be 1/16 of an inch raised above the remainder of the flat surface of the shelf 28 and the clearance above the storage tube 70 when the rack 68 is sitting on the shelf 28 is suitably about 1/4 of an inch. The rather small amount of clearance above the storage tube 70 in the compartment 30 not only conserves storage space within the freezer bay, but also makes it more difficult for the storage rack 68 to become inadvertently displaced even slightly from the compartment 30 even when the storage cassette 24 is tilted slightly or is jarred. As mentioned earlier, the storage cassette 24 shown in the figures includes 26 shelves and stands about six feet long. The heights of the sidewall partitions 46, see e.g. FIG. 4, can be increased or reduced in order to accommodate a fewer or larger number of compartments without changing the overall height of the cassette 24. One would expect microtiter plates to have a shorter profile than tube storage racks, so a cassette 24 configured to store microtiter plates would likely have more compartments 30. It is contemplated that the height of the compartments 30 in any given cassette 24 will normally be the same as one another although this is not a strict requirement of the invention. On the other hand, the height of the cassette 24 from the base where it rests to its top where the cassette puller connects must normally be the same for all cassettes of one system so that the cassette puller can engage the top of the cassettes at a consistent height.

Figure 7:
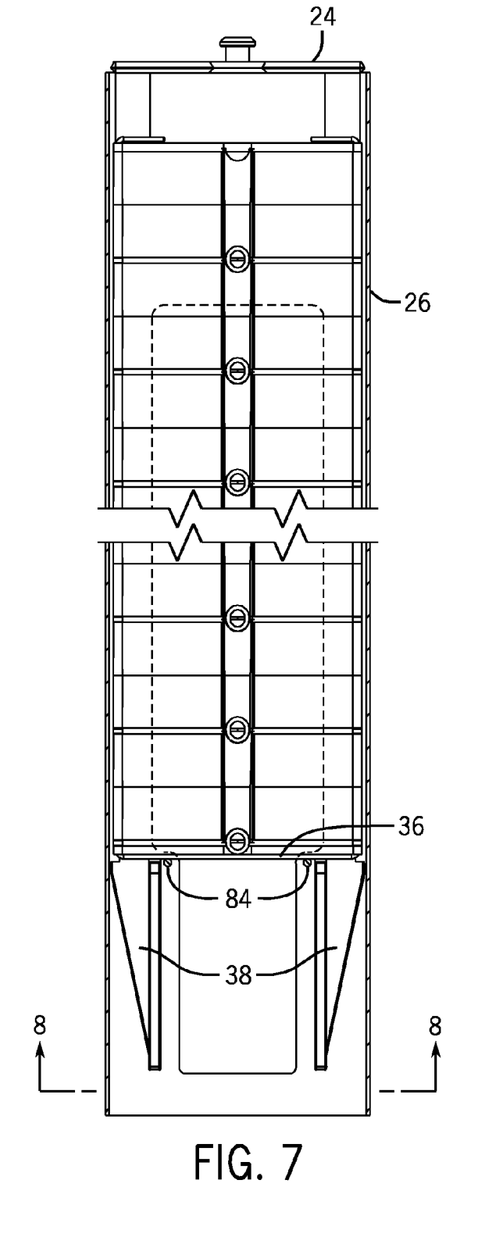
FIG. 7 is a sectional view taken along line 7-7 in FIG. 6 illustrating the exemplary storage cassette tube of FIG. 2 being inserted into the exemplary nesting tube illustrated in FIG. 6.
Figure 8:
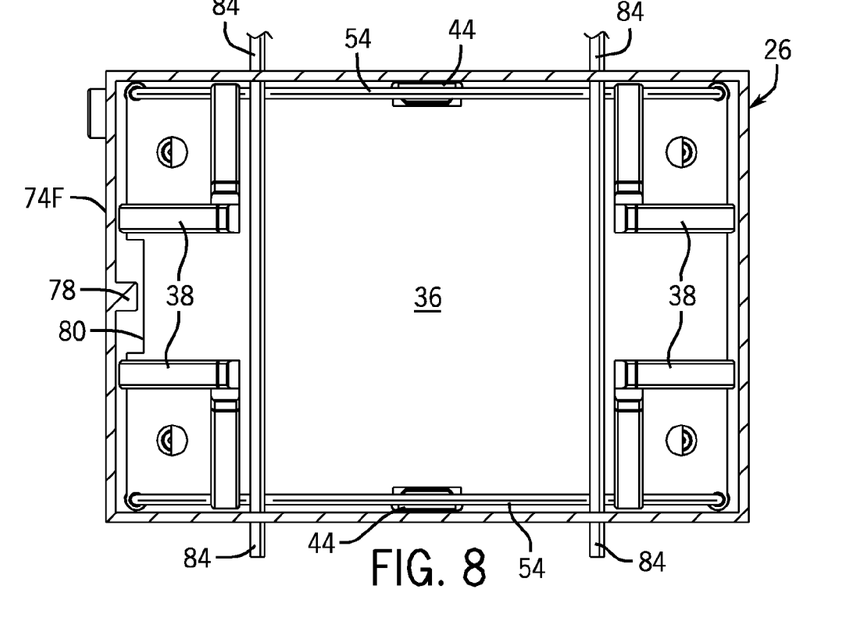
FIG. 8 is a sectional view taken along line 8-8 in FIG. 7.

Referring now to FIGS. 6, 7 and 8, the preferred nesting tubes 26 include sidewalls 74 each having large openings 76 to facilitate air flow in the freezer bay to storage cassettes 24 located in the respective nesting tubes 26. The tubes 26 have a rectangular cross-section commensurate with the cross-section of the cassette 24 and provide ample but not excessive clearance for the cassette 24 within the nesting tube 26. The front side wall of the nesting tube 26 depicted by reference number 74F includes an inwardly extending bar 78 that runs longitudinally substantially the entire length of the tube 26. Referring in particular to FIGS. 4 and 8, the longitudinal bar 78 protrudes inward from the front wall 74F into a longitudinal space created by an indent 80 on the bottom plate 36 of the cassette 24 (FIG. 8) and the indent 82 on the front edge of the shelves 28 (FIG. 4). The purpose of the bar 78 is to prevent storage tube racks and/or plates in the compartments 30 on the cassette 24 from becoming loose when the cassette 24 is located within the nesting tube 26 and being removed or placed into the nesting tube 26.

As mentioned, the nesting tubes 26 are preferably connected together to form a unitary nest 22 placed in the horizontal freezer bay 16, see FIG. 1. It is desirable that the floor of freezer 12 be tilted or contoured in order to facilitate drainage when the freezer 12 is defrosted. It is also desirable in order to facilitate reliable robotic manipulation of the storage cassettes 24 that the caps 56 of the storage cassettes 24 be located at the same height within the nest 22 in the freezer 12. Therefore, it is desirable to support the storage cassette 24 so that the guide legs 38 do not reach the bottom of the respective nesting tube 26 and do not touch the floor of the freezer 12. In the exemplary embodiment shown in the drawings, horizontal support rods 84 extending through each respective row of nesting tubes 26 provide support for each storage cassette 24 at a consistent horizontal height. Referring in particular to FIG. 7, the bottom plate 36 of the storage cassette 24 sits on the horizontal support rods 84 to locate the cassette 24 at a consistent horizontal height below the top of the nesting tube 26 and above the bottom of the freezer floor.

Figure 9:
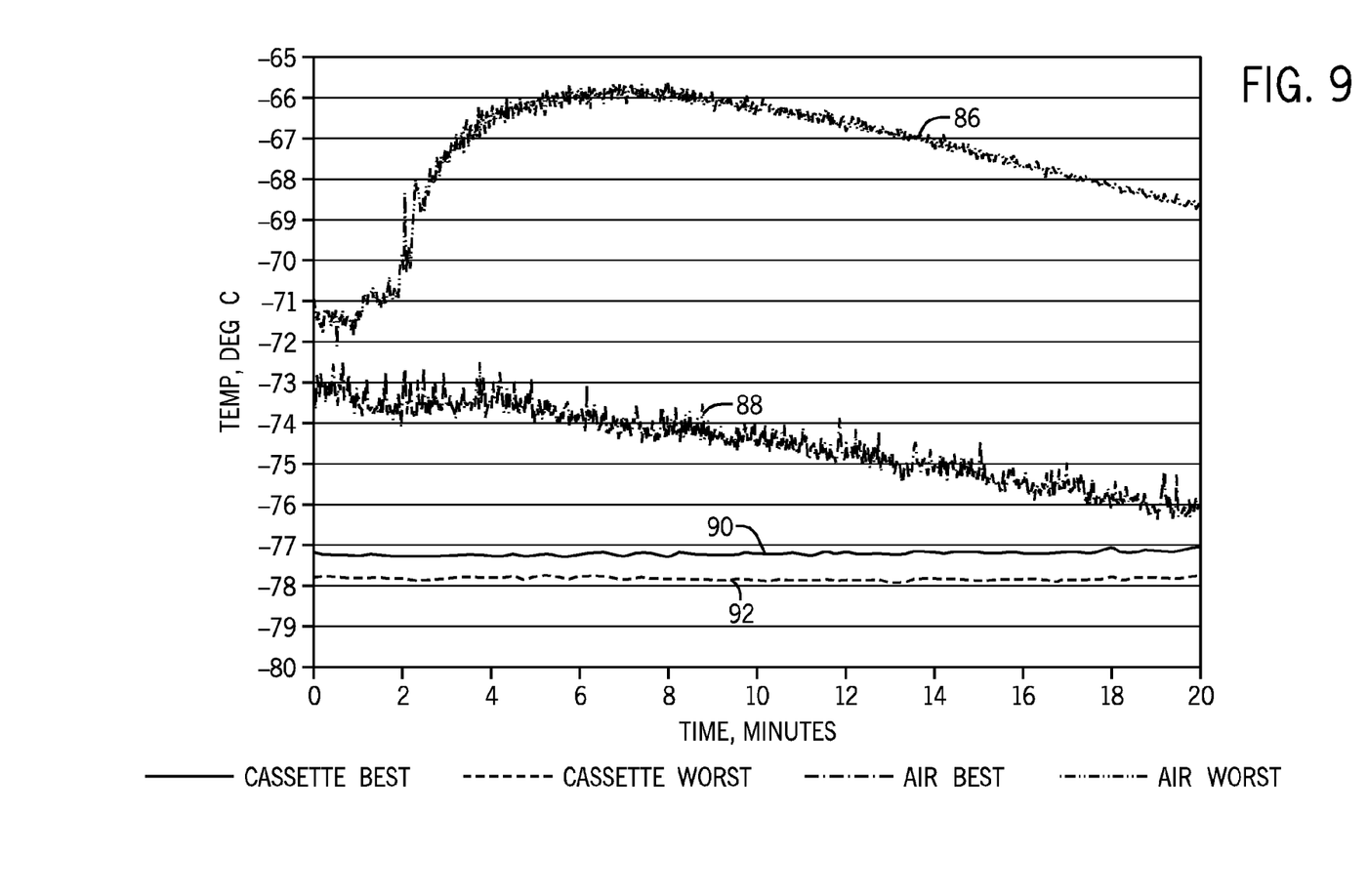
FIG. 9 is a plot of temperature data illustrating that samples in racks stored in cassettes having insulated sidewalls as in accordance with the exemplary embodiment of the invention are subject to less change in temperature than samples in racks without thermal protection.

Temperature data in FIG. 9 shows that a storage cassette 24 with the thermally insulating sidewall partitions 32 and aluminum shelves significantly reduces temperature change of samples stored in a cassette 24. In the test of FIG. 9, temperature probes were placed in water-filled sample tubes placed in a rack. The rack was placed alone in free air in a −80° freezer bay and another nearby cassette with warm samples was added and removed. Data plots 86 and 88 show that the temperature of sample tubes in the rack varied substantially over time when the rack was not placed in an insulating cassette. The test was then run again in the −80° freezer bay with temperature probes in the water-filled tubes placed in the sample storage rack except this time the rack was located in an insulated storage cassette 24 constructed in accordance with the invention. Data plots 90 and 92 show that the temperature change of sample tubes in the rack in the cassette 24 is far less.

Figure 10:
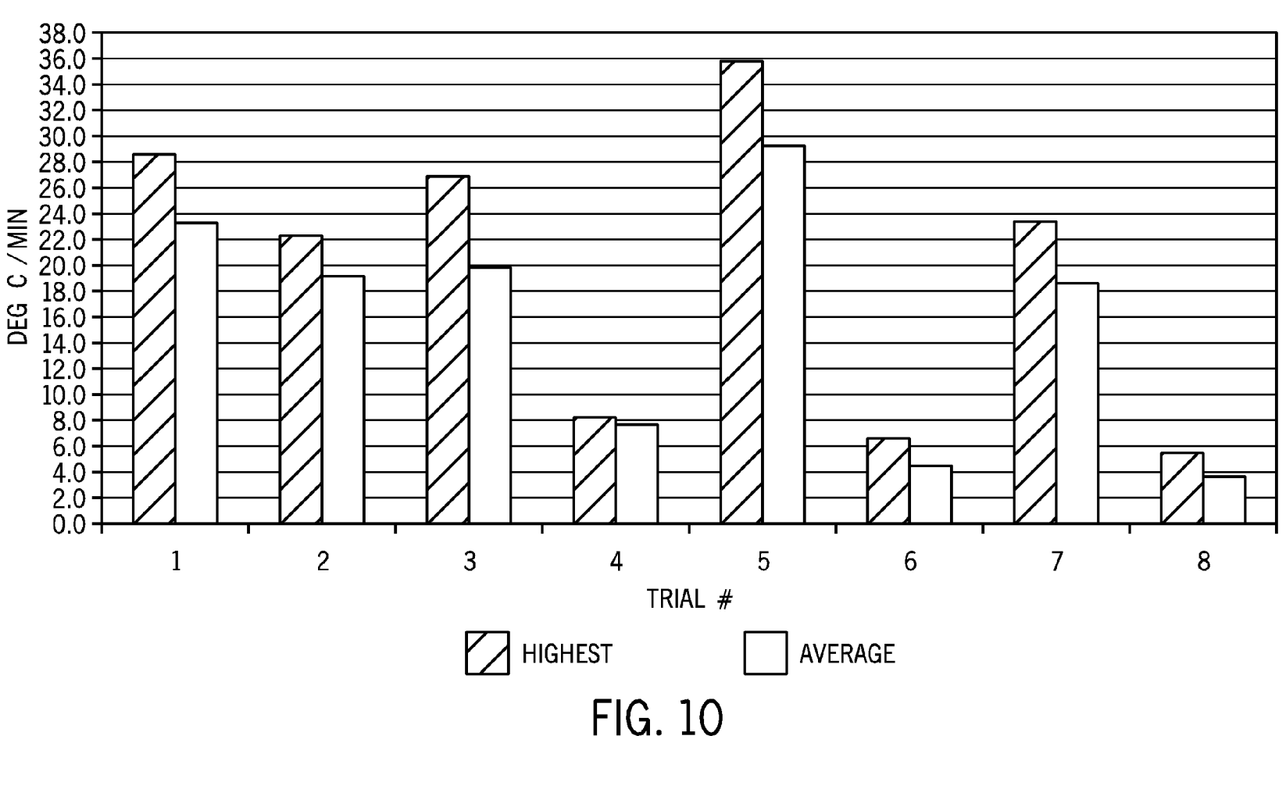
FIG. 10 is a plot of comparative data showing sample tube warm-up rates with racks being placed in storage cassette having various configurations including the configuration of the exemplary embodiment of the invention.

FIG. 10 contains comparative data showing temperature rise in samples stored in racks contained in cassettes having a variety of configurations when the cassettes are removed from a −80° freezer bay. The data plotted is the tube warm-up rate in degrees centigrade per minute. In each test, there were five to eight thermal couples used in different tubes in different locations on the rack. One data bar indicates the highest temperature change rate for the particular cassette configuration and the other data bar indicates average temperature change data for the particular cassette configuration. The tests were conducted by storing the water-filled storage tubes in racks within a cassette in a −80° freezer bay, and then removing the cassette from the freezer and measuring the temperature rise of a sample within a rack in the cassette over time. The cassettes were set on the floor outside of the freezer during the test in a 20° C. environment (i.e. room temperature to simulate worst case condition). The cassette configuration in trial #1 is a conventional open shelf cassette in which the storage rack was placed in a middle shelf on the cassette. The conventional, open shelf cassette in trial #1 does not provide substantial insulation and allows for significant temperature rise, e.g., highest above 28° C. per minute and average above 23° C. per minute. In trial #2, the same conventional, open shelf cassette was used but the storage rack was placed on a top shelf rather than a middle shelf. In trial #3 again the same conventional, open shelf cassette was used, but this time the rack was placed on a bottom shelf. The heat rise is roughly the same for the conventional, open shelf storage cassette in trials 1, 2 and 3 with the temperature rise when the rack is placed on a middle shelf being slightly lower. In trial #4, the rack of water filled tubes was placed in a middle shelf of a conventional, closed-shelf storage cassette. The temperature rise with the closed-shelf cassette in trial #4 is significantly less than with the conventional, open-shelf cassettes; reduced to about 8° C. per minute and this is the case even though the closed-shelf cassette used in trial #4 did not include insulating sidewalls. In trial #5, the same open-shelf cassette as used in trials 1-3 was used, but three sides of the cassette were covered with cardboard simulating the use of three insulated sidewalls. The storage rack was placed on a middle shelf. It is important to note that the placing of the cardboard around the cassette in fact increased the rate of temperature rise. In trial #5 the highest temperature rise was slightly under 36° C. per minute and the average was slightly above 29° C. per minute. It is believed that this increase in temperature rise occurs because of a chimney effect in which warmer air enters near the bottom of the cassette and then rises through the cold air within the cardboard covered cassette thereby pushing out the cold air. Trial #6 used the same configuration as in trial #5 except added a fourth side of cardboard to cover the cassette tightly on all four sides. Note that there is a significant reduction in the rate of temperature rise. In trial #6, the maximum rate of temperature rise was about 6.5° C. per minute and the average was about 4.5° C. per minute. The difference between rate of temperature rise in trials #5 and #6 is due to the addition of the fourth side of cardboard which blocked air flow from entering and rising through the open shelf cassette. Trial #7 used a similar configuration to trials #5 and #6 but in trial #7 the fourth side of cardboard was attached loosely. The rate of temperature rise in trial #7 is significant, this time the highest rate being about 23.5° C. per minute and the average rate being about 18.5° C. per minute. It is believed that the rate of temperature rise increases because warm air is allowed to access into the cassette and push upward throughout the cassette because the cardboard was loosely attached and not tight. In trial #8, a storage rack was placed in one of the middle shelves on a storage cassette constructed in accordance with the invention. It can be seen from the data that the rate of temperature rise in trial #8 using the storage cassette constructed in accordance with the invention is lower than in any of the other trials: about 5.4° C. per minute was the highest rate of temperature rise and the average rate was about 3.6° C. per minute. The storage cassette 24 made in accordance with the invention includes three insulated sides but also includes closed shelves, which block the chimney effect and minimize temperature rise even though the front of the compartments in the storage cassette 24 needs to be open in order to allow access to place and remove the storage racks.

Features of invention have been described above in connection with an exemplary embodiment of the invention. Those skilled in the art will understand that practicing the invention as defined by the appended claims need not require implementation of all of the features described in connection with the exemplary embodiment.

The invention claimed is:

1. A system for holding sample tube storage racks and sample storage plates within a horizontal freezer operating at a temperature of −50° C. or below and for robotically transporting held storage racks and plates into and from the horizontal freezer, the system comprising:

a horizontal freezer operating at a temperature of −50° C. or less and containing a plurality of cassette storage nesting tubes, each nesting tube comprising a vertically oriented rectangular tube to guide a storage cassette over substantially its entire length into the horizontal freezer compartment;

an automated robot for lifting storage cassettes from and lowering storage cassettes into the horizontal freezer;

multiple storage cassettes, each cassette including:

a plurality of generally vertically spaced shelves, each for holding a sample storage rack or plate, the shelves being oriented generally vertical to one another;

separate sidewall partitions made of thermally insulating rigid material located in between the shelves to form a plurality of compartments generally vertical to one another, each compartment containing at least one opening to allow storage racks or plates to be placed in the compartment on the respective shelf and removed from the compartment;

shelf partition plates on which the respective shelves are located;

a top plate and a bottom plate;

a flexible wire for connecting the shelf partition plates and the vertically adjacent sidewall partitions to the top and bottom plates and allowing the storage cassette to bend sufficiently along its vertical axis in order to physically adjust and accommodate dimensional obstructions to avoid jams when being placed into or removed from one of said nesting tubes in the horizontal freezer by the automated robot; and a cap that is located above the compartments and has a retrieval catch adapted to be engaged by the automated robot for lifting and lowering the storage cassette.

2. A system as recited in claim 1 wherein the vertically oriented, rectangular nesting tubes are made of aluminum.

3. A system as recited in claim 1 wherein the plurality of cassette storage nesting tubes are connected to one another to form a unitary nest that fits within the horizontal freezer.

4. A system as recited in claim 1 wherein at least one sidewall on the vertically oriented nesting tubes includes a vertically longitudinal bar that protrudes inward from the sidewall and extends substantially the entire vertical length of the sidewall, wherein the bar maintains storage racks or plates in an appropriate position within the respective compartments of the cassette.

5. A system as recited in claim 1 wherein the spacing between the shelves is chosen so that the vertical travel of a preselected rack of storage tubes having known dimensions or a storage plate having known dimensions is allowed to travel no more than about one-quarter of an inch above a front lip on the respective shelves adjacent to the opening of each compartment.

6. A system as recited in claim 1 wherein the horizontal freezer includes at least one removable lid to provide access by the automatic robot to the top of the storage cassettes.

7. A system as recited in claim 6 wherein the horizontal freezer has two bays and separate removable lids cover each respective bay of the horizontal freezer.

8. A system as recited in claim 1 wherein the respective storage cassettes further comprise tapered, rigid guide legs attached to a bottom of the bottom plate below the plurality of compartments and extending downward from the bottom surface of the bottom plate in order to guide the cassette into the respective vertically oriented, nesting tube; and wherein the plurality of cassette storage nesting tubes are arranged in separate rows, and support rods extend through each row at a height near the bottom of the nesting tubes in order to support the respective storage cassettes so that space exists between rigid guide legs and the floor of the freezer and the bottom of the cassette does not bear weight.

9. A system as recited in claim 8 wherein the floor of the freezer is contoured to facilitate drainage of the freezer when defrosting.

10. A system as recited in claim 1 wherein the caps on the respective storage cassettes each include a top plate having an upwardly extending retrieval catch and upwardly facing guide holes for accepting locator pins on the automated transfer robot.

11. A system as recited in claim 1 wherein the respective storage cassettes further comprise tapered, rigid guide legs attached to a bottom of the bottom plate below the plurality of compartments and extending downward from the bottom surface of the bottom plate in order to guide the cassette into the respective vertically oriented, nesting tube; and the tapered, rigid guide legs each comprise at least one straight, inclined surface extending between a lower end positioned inside the perimeter of the bottom plate and an upper end positioned to be aligned with the perimeter of the bottom plate.

12. A system as recited in claim 1 wherein an outside surface of the respective storage cassettes include position referencing stops for each compartment in the respective cassette and the system further comprises the automated robot that uses the referencing stops to verify and adjust the precise location of the storage cassette once it has been removed from the freezer and presented in a location for the removal of a tube rack or plate from or placement into a respective compartment in the cassette.

13. A system as recited in claim 1 wherein sidewalls of the nesting tubes contain air flow openings over a substantial portion of the surface area of the respective tube sidewalls.

14. A system as recited in claim 1 wherein the flexible wire holds the spaced apart shelf partition plates and vertically adjacent sidewall partitions along the respective corners of the shelf partition plates and wall partitions.

15. A system as recited in claim 14 wherein the flexible wire includes a first strand of flexible wire and a second strand of flexible wire connect the shelf partition plates and the vertically adjacent sidewall partitions to the top and bottom plates, and the ends of the first and second strands are secured the top plate or cap of the cassette and each strand passes through openings in the corners of the bottom plate.

16. A system as recited in claim 1 wherein the cassette shelves are planar from edge to edge without openings.

17. A system as recited in claim 16 wherein the shelves are made of aluminum.

18. A system as recited in claim 1 wherein the cassette shelves forming the floors of the respective compartments are substantially rectangular and planar from edge to edge without openings and the thermally insulated sidewall partitions cover substantially three sides of the respective compartments.

19. A system as recited in claim 1 wherein the cap on each cassette above the plurality of compartments is an insulated cap.

20. A system as recited in claim 1 wherein at least one storage cassette further comprising means for guiding the bottom of the storage cassette as it is placed into one of the respective nesting tubes.

* * * * *